United States Patent
Foguet et al.

[11] Patent Number: 5,798,361
[45] Date of Patent: Aug. 25, 1998

[54] 5H-THIAZOLO[3,2-A]PYRIMIDIN-5-ONE DERIVATIVES

[75] Inventors: Rafael Foguet; Lluis Anglada; Aurelio Sacristan; Josep M. Castello; Jose A. Ortiz, all of Barcelona, Spain

[73] Assignee: Ferrer Internacional, S.A., Barcelona, Spain

[21] Appl. No.: 765,935

[22] PCT Filed: May 24, 1996

[86] PCT No.: PCT/EP96/02254

§ 371 Date: Mar. 14, 1997

§ 102(e) Date: Mar. 14, 1997

[87] PCT Pub. No.: WO96/37498

PCT Pub. Date: Nov. 28, 1996

[30] Foreign Application Priority Data

May 26, 1995 [ES] Spain ................. 9501029

[51] Int. Cl.$^6$ .................. A61K 31/505; C07D 513/04
[52] U.S. Cl. ........................... 514/258; 544/278
[58] Field of Search .................. 544/278; 514/258

[56] References Cited

U.S. PATENT DOCUMENTS 4,443,451  4/1984  Kennis ................. 544/252

FOREIGN PATENT DOCUMENTS 196132  10/1986  European Pat. Off.
94-01437  1/1994  WIPO.

OTHER PUBLICATIONS

Pash, Chem Abs 93, 239357 (1980).

*Primary Examiner*—Mark L. Berch
*Attorney, Agent, or Firm*—Birch, Stewart, Kolasch & Birch, LLP

[57] ABSTRACT

The present invention relates to new 5H-thiazolo[3,2-a] pyrimidin-5-one derivatives having the formula (I):

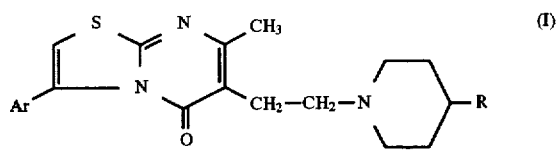

wherein Ar is phenyl optionally substituted by one or two groups selected from halogen, alkyl having from 1 to 4 carbon atoms, methylendioxy, alkoxy having from 1 to 4 carbon atoms, and trifluoromethyl; and R is a group selected from (a) or (b):

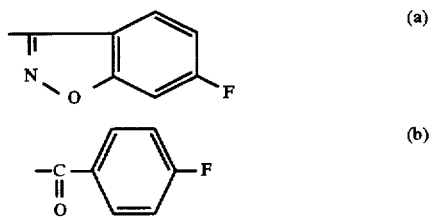

as well as their pharmaceutically acceptable addition salts, which are useful in the treatment of psychosis, schizophrenia and anxiety. This invention also discloses methods and intermediates for their preparation and pharmaceutical compositions containing them.

7 Claims, No Drawings

5H-THIAZOLO[3,2-A]PYRIMIDIN-5-ONE DERIVATIVES

The present invention relates to new 5H-thiazolo[3,2-a]pyrimidin-5-one derivatives having the formula (I):

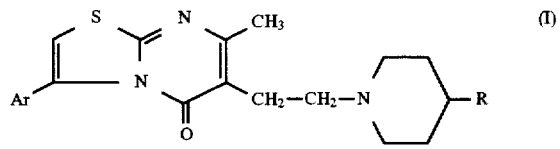

wherein Ar is phenyl optionally substituted by one or two groups selected from halogen, alkyl having from 1 to 4 carbon atoms, methylendioxy, alkoxy having from 1 to 4 carbon atoms, and trifluoromethyl; and R is a group selected from (a) or

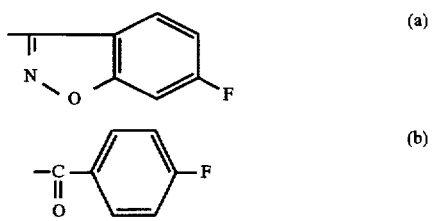

or a pharmaceutically acceptable addition salt thereof which are useful for the treatment of psychosis, schizophrenia and anxiety.

The compounds of the present invention are obtained by reacting 3-aryl-6-(2-substituted ethyl)-7-methyl-thiazolo[3,2-a]pyrimidin-5-one of general formula (II), wherein Ar is as defined for (I) and X is a halogen selected from chlorine, bromine or iodine, or a sulfonyloxy group, e.g., methylsulfonyloxy, p-toluensulfonyloxy and the like, with a piperidine of general formula (III) wherein R is as defined for (I) according to Scheme 1:

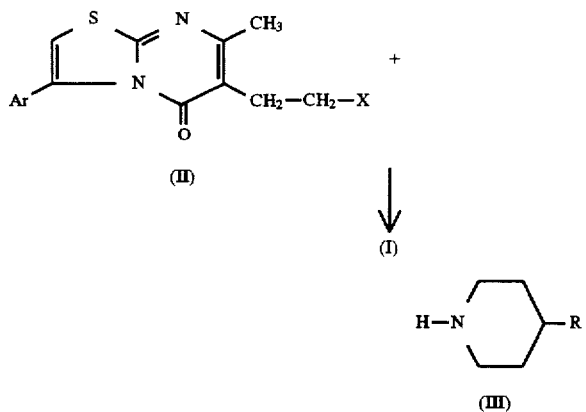

The reaction can conveniently be conducted in an inert organic solvent such as, for example, N,N-dimethylformamide, N,N-dimethylacetamide, acetonitrile and the like, and in the presence of a base such as, for example, alkali metal carbonates, acid carbonates, alkoxides or hydrides. The addition of catalytic amounts of an alkali metal iodide enhances the reaction.

In turn, the intermediates of general formula (II) are prepared by reacting the corresponding 4-aryl-2-thiazolamines of general formula (IV), wherein Ar is as defined for the foregoing structures, with 2-acetylbutyrolactone, and then by halogenation or sulfonation of 3-aryl-6-(2-hydroxyethyl)-7-methyl-thiazolo[3,2-a]pyrimidin-5-ones (V) according to Scheme 2:

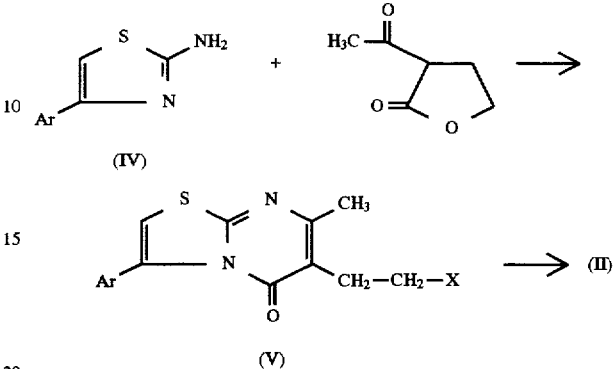

The foregoing procedure may occasionally be carried out without isolating the intermediates of general formula (V). Standard halogenating agents which may be used for the halogenation of (V) include phosphorus oxychloride, phosphorus oxybromide, phosphorus trichloride, phosphorus tribromide, phosphorus pentachloride, phosphorus pentabromide, thionyl chloride, t-butyl hypochlorite and the like. Standard sulfonating agents which may be used for the sulfonation of (V) include methylsulfonyl chloride, p-toluensulfonyl chloride and the like.

The intermediates of general formula (II) when X is chlorine will be hereinafter designated with the general formula (VI):

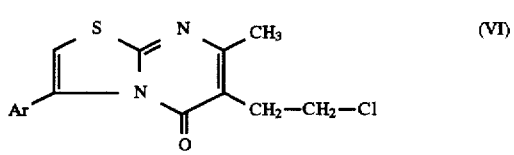

wherein Ar is as defined for the foregoing structures. These compounds are very appropriate for the procedure in Scheme 2. Due to the fact that such new intermediates are described for the first time, the scope of the present invention will also be referred to them.

As the background of the present invention there are cited European Patent No. 0196132 where the preparation of 1,2-benzisoxazol-3-yl and 1,2-benzisothiazol-3-il derivatives, and their use in the treatment of psychotic diseases and of those other diseases which serotonin release is of predominant importance are described; and U.S. Pat. No. 4,443,451 where the preparation of bicyclic pyrimidin-5-one derivatives and their use as psychotropic agents are described.

The biochemical assays demonstrate that the compounds of the present invention possess a strong activity on receptors involved in the neuroleptic action ($D_2$ and $5HT_2$) (B. A. McMillen et al., "Drug Dev. Res.", 12, 53–62, 1988).

Specific binding to $D_2$ and $5HT_2$ receptors was tested as follows:

$D_2$ receptors: A 2-nM solution of radioactive spiperone ([$^3$H]spiperone), which acts as a specific ligand, was incubated with the membrane corresponding to 20 mg of rat striatum for 20 min at 35° C. buffered at pH 7.4 with Tris.HCl. The non-specific binding was then determined by addition of a micromolar concentration of unlabelled spiperone. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

$5HT_2$ receptors: A 0.5 nM solution of radioactive ketanserin ($[^3H]$ketanserin), which acts as a specific ligand, was incubated with the membrane corresponding to 1 mg of rat cortex for 30 min at 35° C. buffered at pH 7.4 with Tris.HCl. Non-specific binding was then determined by addition of 5 micromolar concentration of unlabelled mianserin. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

The results from the specific binding to $D_2$ and $5HT_2$ receptors are presented as $IC_{50}$ (M) in Table 1.

TABLE 1

| | | $IC_{50}$ (M) | | |
|---|---|---|---|---|
| Code | Compound (I) | $D_2$ | $5HT_2$ | $D_2/HT_2$ |
| FI-8510 | Example 14 | $1.97 \times 10^{-8}$ | $3.18 \times 10^{-9}$ | 6.2 |
| FI-8525 | Example 15 | $4.41 \times 10^{-8}$ | $3.94 \times 10^{-9}$ | 11.2 |
| FI-8542 | Example 16 | $4.21 \times 10^{-8}$ | $8.32 \times 10^{-9}$ | 5.1 |
| FI-8544 | Example 17 | $3.64 \times 10^{-8}$ | $1.49 \times 10^{-8}$ | 2.4 |
| FI-8543 | Example 18 | $1.73 \times 10^{-8}$ | $7.63 \times 10^{-9}$ | 2.3 |
| FI-8545 | Example 19 | $4.36 \times 10^{-8}$ | $1.11 \times 10^{-8}$ | 3.9 |
| FI-8546 | Example 20 | $1.94 \times 10^{-8}$ | $3.52 \times 10^{-8}$ | 0.6 |
| FI-8568 | Example 21 | $1.66 \times 10^{-8}$ | $2.45 \times 10^{-8}$ | 0.7 |
| FI-8570 | Example 22 | $2.80 \times 10^{-8}$ | $7.46 \times 10^{-9}$ | 3.8 |
| FI-8569 | Example 23 | $2.23 \times 10^{-8}$ | $3.21 \times 10^{-8}$ | 0.7 |
| FI-8567 | Example 24 | $2.92 \times 10^{-8}$ | $2.95 \times 10^{-8}$ | 1.0 |
| FI-8571 | Example 25 | $2.09 \times 10^{-8}$ | $8.33 \times 10^{-8}$ | 0.3 |
| FI-8572 | Example 26 | $8.20 \times 10^{-8}$ | $3.51 \times 10^{-9}$ | 23.4 |
| FI-8547 | Example 27 | $1.74 \times 10^{-7}$ | $1.25 \times 10^{-8}$ | 13.9 |
| FI-8548 | Example 28 | $7.99 \times 10^{-8}$ | $8.26 \times 10^{-9}$ | 9.7 |
| | Haloperidol | $1.39 \times 10^{-8}$ | $1.04 \times 10^{-7}$ | 0.1 |

From the results of the above table, it can be concluded that the compounds of this invention are characterized by a genuine neuroleptic profile as a result of their specificity on $5HT_2$ receptors against $D_2$ receptors according to $D_2/5HT_2$ ratios which is advantageously higher than that of Haloperidol. This provides the compounds with little possibility to cause extrapyramidal effects at the therapeutic doses.

In Animal Pharmacology Studies, the antipsychotic activity of the compounds was tested by the inhibition of apomorphine-induced climbing behaviour (P.Protais et al: "Psychopharmacology", 50, 1–6, 1976), and their activity on $5HT_2$ receptors by the inhibition test of 1-(2,5-dimethoxy-4-iodophenyl)-2-aminopropane (DOI)-induced head twitches and scratches (M. Oka et al: "J. Pharm. Exp. Ther.", 264(1), 158–165, 1993). The inhibiton test of apomorphine-induced climbing behaviour and the inhibition test of DOI-induced head twitches and scratches are hereinafter described.

Inhibition of aoomorphine-induced climbing behaviour

Male Swiss mice weighing 22–24 g were used. One week prior to experiment, animals were kept in our facilities at a temperature of 20°–22° C. and 12/12 h light-dark cycle, and had free access to food and water. Two hours prior to experiment, the animals were placed in individual cages without access to food.

Animals were administered orally with test drug or 0.25% agar at time 0. After 60 minutes, apomorphine was subcutaneously injected at a dose of 1 mg/kg, and after further 70 minutes the animal's behaviour was assessed. Two additional assessments were performed at 10-min intervals. For assessment, each animal was placed on the bottom of a small upright box (11×7.5×4.5 cm). The walls of the box were made of translucent methacrylate except one of the lateral surfaces (7.5 cm wide) which was a 3-mm wire mesh. The position of the animal was scored for 2 minutes according to the following criteria: 0=four paws on the floor; 1=three paws on the floor; 2=two paws on the floor; 3=one paw on the floor; and 4=four paws holding the wire mesh. If an animal keeps several positions within the 2-min observation, the seconds elapsed in each position will be recorded. Finally, mean scoring was calculated. Under these experimental conditions, the effective dose 50% ($ED_{50}$) values are shown in Table 2.

Inhibition of DOI-induced head twitches and scratches

Male N.M.R.I. mice weighing 22–26 g were used. After the animals were weighed, they were individually placed in transparent cages two hours prior to experiment. Test compound was given p.o. at time 0. The administration interval time between mice was 5 min. At time 60 min DOI at the dose of 3 mg/kg i.p. dissolved in saline was administered. The number of head twitches and scratches were assessed as well as the presence or absence of escape attempts. The effective dose 50% ($ED_{50}$) values obtained under the above experimental conditions are shown in Table 2.

Similarly, it was proved that by oral route in Sprague-Dawley rats, 50% of treated animals showed catalepsy ($ED_{50}$, mg/kg) according to the values in Table 2.

TABLE 2

| | | $ED_{50}$ (mg/kg) | | | |
|---|---|---|---|---|---|
| Code | Compound (I) | Climbing | DOI | Catalepsy | R* |
| FI-8510 | Example 14 | 2.9 | 0.28 | 9.3 | 3.2 |
| FI-8525 | Example 15 | 14.7 | 0.58 | 16 | 1.1 |
| FI-8542 | Example 16 | 7.4 | 0.84 | 30 | 4.1 |
| FI-8544 | Example 17 | 3.9 | 0.57 | 22.5 | 5.8 |
| FI-8543 | Example 18 | 7.7 | 0.80 | 20 | 2.6 |
| FI-8545 | Example 19 | 3.5 | 0.82 | 9.5 | 2.7 |
| FI-8570 | Example 22 | 19.0 | 1.10 | 40 | 2.1 |
| FI-8567 | Example 24 | >50 | 1.50 | >50 | — |
| FI-8572 | Example 26 | >50 | 0.42 | >50 | — |
| FI-8547 | Example 27 | >50 | 1.20 | >50 | — |
| FI-8548 | Example 28 | 24.6 | 0.60 | >50 | >2.0 |
| | Haloperidol | 1.2 | 1.5 | 1.95 | 1.6 |

*R = Catalepsy/Climbing

According to the above table and on the basis of the Catalepsy/Binding (R) ratio, some compounds of the present invention surprisingly exhibit a higher therapeutic margin than that of Haloperidol, which makes them be potentially safer. This fact confirms the higher selectivity of the compounds in $5HT_2$ receptors against $D_2$ receptors found in the biochemical assays. Furthermore, in another independent pharmacological study, anti-DOI test, the pharmacological action on $5HT_2$ receptors was higher in several compounds of the present invention than in Haloperidol.

EXAMPLE 1

3-(4-methylphenyl)-6-(2-chloroethyl)-7-methylthiazolo[3,2-a]pyrimidin-5-one 5.7 g (30 mmoles) of 2-amino-4-(4-methylphenyl)-thiazol were dissolved in 11 ml (120 mmoles) of phosphorus oxychloride. To the solution formed, 3.25 ml (30 mmoles) of 2-acetyl-butyrolactone were slowly added. The mixture was refluxed for 2 hours, allowed to cool and poured onto 100 g of ice, then basified to pH 9 by adding sodium hydroxide and extracted twice with 100 ml of methylene chloride each time. The organic phase was washed twice with 50 ml of water each time and dried, and the solvent was removed by reduced pressure distillation. The residue formed was purified on a silica gel column using methylene chloride as eluent. 3.4 g of 3-(4-methylphenyl)-6-(2-chloroethyl)-7-methyl-thiazolo[3,2-a]pyrimidin-5-one were obtained as a yellowish solid, mp 152°–165° C.

EXAMPLES 2–13

Following the same procedure as for the compound in Example 1 and starting from appropriate 4-aryl-2-thiazol-amines, 3-aryl-6-(2-chloroethyl)-7-methylthiazolo[3,2-a]pyrimidin-5-ones in Table 3 were obtained.

TABLE 3

| Compound (VI) | Ar | mp °C. |
|---|---|---|
| Example 2 | 4-fluorophenyl | 155.8–158 |
| Example 3 | phenyl | 134.5–136.4 |
| Example 4 | 4-methoxyphenyl | 150.7–152.5 |
| Example 5 | 4-chlorophenyl | 161–163.5 |
| Example 6 | 3,4-dichlorophenyl | 124–128 |
| Example 7 | 3-chlorophenyl | 105–110 |
| Example 8 | 3-methoxyphenyl | 129–132 |
| Example 9 | 3-methylphenyl | 97–101 |
| Example 10 | 3-trifluoromethylphenyl | 128–129.5 |
| Example 11 | 2-fluorophenyl | 160–164 |
| Example 12 | 3-benzo[1,3]dioxol-5-yl | 179–185.2 |
| Example 13 | 2-chlorophenyl | 210–213 |

EXAMPLE 14

6-[2-[4-(6-fluoro-1,2-benzisoxazol-3-yl)-1-piperidinyl]ethyl]-3-(4-fluorophenyl)-7-methyl-5H-thiazolo[3,2-a]pyrimidin-5-one (FI-8510)

In 190 ml of N,N-dimethylformamide, 13.3 g (41.2 mmoles) of 3-(4-fluorophenyl)-6-(2-chloroethyl)-7-methyl-thiazol [3,2-a]pyrimidin-5-one, 9.1 g (41.2 mmoles) de 6-fluoro-3-(4-piperidinyl)-benzisoxazol, 18.2 g (131.7 mmoles) of potassium carbonate and a catalytic amount of potassium iodide were suspended. The reaction mixture was heated for 18 hours at a temperature ranging between 85° and 90° C., cooled to 20° C. and poured into 400 ml of water. The solid formed was purified on silica gel column, using acetonitrile/methanol as eluent. 8.5 g of 6-[2-[4-(6-fluoro-1,2-benzisoxazol-3-yl)-1-piperidinyl]ethyl]-3-(4-fluorophenyl)-7-methyl-5H-thiazolo[3,2-a]pyrimidin-5-one were obtained, mp 119°–122° C.

EXAMPLE 15

6-[2-[4-(6-fluoro-1,2-benzisoxazol-3-yl)-1-piperidinyl]ethyl]-3-phenyl-7-methyl-5H-thiazolo[3,2-a]pyrimidin-5-one (FI-8525)

In 50 ml de N,N-dimethylformamide, 3.12 g (10.2 mmoles) of 3-phenyl-6-(2-chloroethyl)-7-methyl-thiazolo[3,2-a]pyrimidin-5-one, 2.23 g (10.2 mmoles) of 6-fluoro-3-(4-piperidinyl)-benzisoxazol, 4.50 g (32.5 mmoles) of potassium carbonate and a catalytic amount of potassium iodide were suspended. The reaction mixture was heated for 18 hours at a temperature ranging between 85° and 90° C., cooled to 20° C. and poured into 100 ml of water. The solid formed was purified on silica gel column, using acetonitrile/methanol as eluent. 2.1 g of 6-[2-[4-(6-fluoro-1,2-benzisoxazol-3-yl)-1-piperidinyl]ethyl]-3-phenyl-7-methyl-5H-thiazolo[3,2-a]pyrimidin-5-one, mp 76°–91° C.

EXAMPLE 16

6-[2-[4-(6-fluoro-1,2-benzisoxazol-3-yl)-1-piperidinyl]ethyl]-3-(4-methoxyphenyl)-7-methyl-5H-thiazolo[3,2-a]pyrimidin-5-one (FI-8542)

In 20 ml of acetonitrile, 1.34 g (4 mmoles) of 3-(4-methoxyphenyl)-6-(2-chloroethyl)-7-methyl-thiazolo[3,2-a]pyrimidin-5-one, 1.03 g (4 mmoles) piperidinyl)-benzisoxazol hydrochloride, 2.21 g (16 mmoles) of potassium carbonate and a catalytic amount of potassium iodide were suspended. The reaction mixture was refluxed for 18 hours, cooled to 20° C. and filtered, and the filtrate was evaporated by reduced pressure distillation. Purification of the crude was performed on silica gel column using acetonitrile/methanol as eluent. 15 g of 6-[2-[4-(6-fluoro-1,2-benzisoxazol-3-yl)-1-piperidinyl]ethyl]-3-(4-methoxyphenyl)-7-methyl-5H-thiazolo[3,2-a]pyrimidin-5-one, mp 113.5°–118.9° C.

EXAMPLES 17–28

Following the same procedure as for the compound in Example 16 and starting from appropriate intermediates, the compounds in Table 4 were obtained.

TABLE 4

| Code | Cpds. (I) | Ar | R | mp °C. |
|---|---|---|---|---|
| FI-8544 | Example 17 | 4-methylphenyl | a | 75–119 |
| FI-8543 | Example 18 | benzo[1,3]dioxol-5-yl | a | 209–213 |
| FI-8545 | Example 19 | 4-chlorophenyl | a | 79–98 |
| FI-8546 | Example 20 | 3,4-dichlorophenyl | a | 86–114 |
| FI-8568 | Example 21 | 3-chlorophenyl | a | 70–102 |
| FI-8570 | Example 22 | 3-methoxyphenyl | a | 71–111 |
| FI-8569 | Example 23 | 3-methylphenyl | a | 77–93 |
| FI-8567 | Example 24 | 2-chlorophenyl | a | 84–93 |
| FI-8571 | Example 25 | 3-trifluoromethylphenyl | a | 75–94 |
| FI-8572 | Example 26 | 2-fluorophenyl | a | 71–91 |
| FI-8547 | Example 27 | phenyl | b | 65–86 |
| FI-8548 | Example 28 | 4-methoxyphenyl | b | 66–78 |

EXAMPLE 29

Injectable solution
  Formulation for 1 ampoule:
    6-[2-[4-(6-fluoro-1,2-benzisoxazol-3-yl)-1-piperidinyl]ethyl]-3-(4-fluorophenyl)-7-methyl-5H-thiazolo[3,2-a]pyrimidin-5-one 5.0 mg methyl p-hydroxybenzoate 1.0 mg propyl p-hydroxybenzoate 0.1 mg Bidistilled water q.s. 2.0 ml

EXAMPLE 30

1% oral solution
    6-[2-[4-(6-fluoro-1,2-benzisoxazol-3-yl)-1-piperidinyl]ethyl]-3-(4-fluorophenyl)-7-methyl-5H-thiazolo[3,2-a]pyrimidin-5-one 1000 mg methyl p-hidroxibenzoato 135 mg propyl p-hidroxibenzoato 15 mg Sorbitol 70% 20 g Sodium saccharin 50 mg Orange essence 0.25 ml Distilled water q.s. 100 ml

EXAMPLE 31

Tablets
  Formulation for 10 mg tablet:
    6- [2- [4-(6-fluoro-1,2-benzisoxazol-3-yl)-1-piperidinyl]ethyl]-3-(4-methylphenyl)-7-methyl-5H-thiazolo[3,2- a]pyrimidin-5-one 10.0 mg Corn starch 43.2 mg Talc 6.0 mg Hydrogenated castor oil 2.0 mg Lactose q.s. 200.0 mg

EXAMPLE 6

Tablets
Formulation for 50 mg tablet:
6-[2-[4-(6-fluoro-1,2-benzisoxazol-3-yl)-1-piperidinyl] ethyl]-3-(4-methylphenyl)-7-methyl-5H-thiazolo[3,2-a]pyrimidin-5-one 50.0 mg Corn starch 86.4 mg Talc 12.0 mg Hydrogenated castor oil 4.0 mg Lactose q.s. 400.0 mg

We claim:

1. A 5H-thiazolo[3,2-a]pyrimidin-5-one derivative having the formula (I):

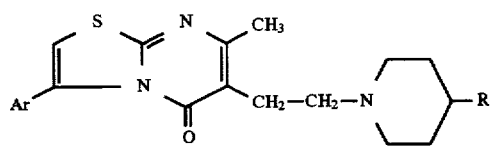
(I)

wherein Ar is phenyl optionally substituted by one or two groups selected from halogen, alkyl having from 1 to 4 carbon atoms, methylendioxy, alkoxy having from 1 to 4 carbon atoms, and trifluoromethyl; and R is a group selected from (a) or (b):

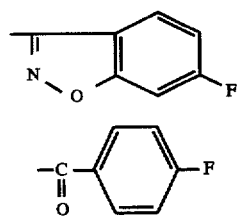

or a pharmaceutically acceptable acid addition salt thereof.

2. A 5H-thiazolo[3,2-a]pyrimidin-5-one derivative compounds of formula (VI):

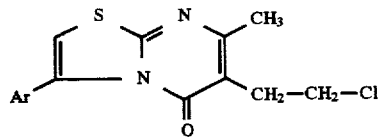
(VI)

wherein Ar is phenyl optionally substituted by one or two groups selected from halogen, alkyl having from 1 to 4 carbon atoms, methylendioxy, alkoxy having from 1 to 4 carbon atoms, and trifluoromethyl; or a pharmaceutically acceptable acid addition salt thereof.

3. A pharmaceutical composition comprising an effective amount of compound of claim 1 to treat psychosis, schizophrenia or anxiety; and a pharmaceutically acceptable carrier.

4. A method of treatment of psychosis, schizophrenia or anxiety which comprises administering to a mammal in need thereof an effective amount of a compound according to claim 1.

5. A process for preparing a 5H-thiazolo[3,2-a]pyrimidin-5-one or a pharmaceutically acceptable acid addition salt thereof according to claim 1, which comprises reacting 3-aryl-6-(2-substituted ethyl)-7-methyl-thiazolo[3,2-a] pyrimidin-5-one of formula (II):

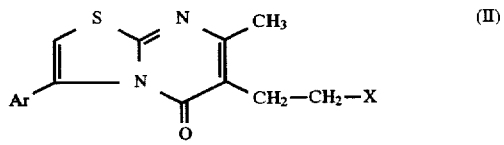
(II)

wherein Ar is phenyl optionally substituted by one or two groups selected from halogen, alkyl having from 1 to 4 carbon atoms, methylendioxy, alkoxy having from 1 to 4 carbon atoms, and trifluoromethyl; and X is a halogen selected from chlorine, bromine or iodine, or a sulfonyloxy group selected from methylsulfonyloxy or p-toluenesulfonyloxy, with a piperidine of formula (III):

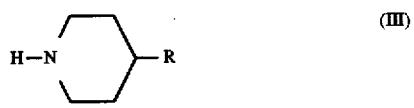
(III)

wherein R is a group selected from (a) or (b):

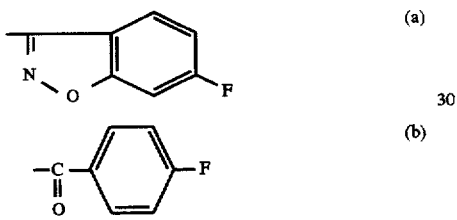

6. A process for preparing a 5H-thiazolo[3,2-a]pyrimidin-5-one derivative of claim 2 which comprises chlorinating a compound of formula (V)

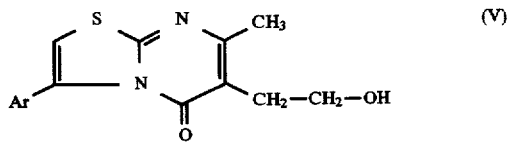
(V)

wherein Ar is phenyl optionally substituted by one or two groups selected from halogen, alkyl having from 1 to 4 carbon atoms, methylendioxy, alkoxy having from 1 to 4 carbon atoms, and trifluoromethyl.

7. The process according to claim 5 wherein X is methylsulfonyloxy or p-toluenesulfonyloxy.

* * * * *